United States Patent [19]

Higley et al.

Best Available Copy

[11] E Re. 30,856

[45] Reissued Jan. 26, 1982

[54] POLYCARBONATE MEMBRANES AND PRODUCTION THEREOF

[75] Inventors: Willard S. Higley, Glendora; Paul A. Cantor, Los Angeles; Bruce S. Fisher, Covina, all of Calif.

[73] Assignee: United States of America, Washington, D.C.

[21] Appl. No.: 119,229

[22] Filed: Feb. 7, 1980

Related U.S. Patent Documents

Reissue of:

[64] Patent No.: 4,075,108
Issued: Feb. 21, 1978
Appl. No.: 636,062
Filed: Nov. 28, 1975

U.S. Applications:

[63] Continuation-in-part of Ser. No. 454,939, Mar. 26, 1974, abandoned.

[51] Int. Cl.[3] ..... B29D 27/00
[52] U.S. Cl. ..... 264/41; 210/500.2
[58] Field of Search ..... 264/41; 210/500.2

[56] References Cited

U.S. PATENT DOCUMENTS

| | | | |
|---|---|---|---|
| 3,133,132 | 5/1964 | Loeb et al. | 264/49 |
| 3,332,894 | 7/1967 | Cantor et al. | 264/41 X |
| 3,767,737 | 10/1973 | Lundstrom | 264/41 |

OTHER PUBLICATIONS

Goldberg, Eugene P., "Journal of Polymer Science", Part C, No. 4, pp. 707–730 (1963).

U.S. Department of Health, Education and Welfare, "Proceedings of the 5th Annual Contractor's Conference of the National Institute of Arthritis and Metabolic Diseases", (1972), pp. 32–33.

Billmeyer, Fred. W., "Textbook of Polymer Science", New York, Interscience, ©1962, pp. 79–86.

*Primary Examiner*—Philip Anderson

*Attorney, Agent, or Firm*—Lerner, David, Littenberg & Samuel

[57] ABSTRACT

Polycarbonate membranes useful for hemodialysis are fabricated from polyether-polycarbonate block copolymers by a water gelation process. The process comprises casting onto a substrate surface a layer of a multicomponent casting solution comprising the copolymer dissolved in a water-miscible organic solvent together with a cosolvent which acts as a swelling agent for the copolymer, drying the layer to partially evaporate the solvents therefrom, immersing the partially dried layer in water to form a gelled membrane, and stripping the gelled membrane from the substrate surface. The membrane has improved strength and improved permeability to solutes in the "middle molecule" range while maintaining clinically acceptable ultrafiltration rates and clearance of low molecular weight solutes.

25 Claims, No Drawings

POLYCARBONATE MEMBRANES AND PRODUCTION THEREOF

Matter enclosed in heavy brackets [ ] appears in the original patent but forms no part of this reissue specification; matter printed in italics indicates the additions made by reissue.

This application is a continuation-in-part of our earlier copending application Ser. No. 454,939, filed Mar. 26, 1974, and now abandoned.

The invention described herein was developed under contract (NIH-70-2100) from the U.S. Public Health Service, Department of Health, Education and Welfare.

This invention relates to new and improved polycarbonate membranes and their production, and particularly to such membranes which are especially useful for hemodialysis.

Hemodialysis membranes for use in the artificial kidney are at the present time generally made of cellophane materials. The best of these materials currently available for such purpose has been found to be a cellulose regenerated from a cuproammonium solution, plasticized with glycerol and identified by the trademark "Cuprophan". Although Cuprophan membranes provide ultrafiltration rates and clearance of low molecular weight solutes within the desirable ranges for proper hemodialysis, they still have many deficiencies which prevent them from being completely satisfactory as hemodialysis membranes. Certain toxins which it is thought necessary to remove from the blood by hemodialysis are "middle molecules", i.e., molecules of molecular weights in the range of 300 to 5,000. Such middle molecules pass through Cuprophan membranes at rates much slower than is desirable. Additionally, the burst and tear strengths of Cuprophan membranes are lower than is desirable in materials employed in hemodialysis and their shelf-life is low, apparently due to migration of plasticizer during storage. Further, the permeability of the Cuprophan membranes has been found to vary from batch to batch and to decrease on ageing. Lastly, it is very difficult to cause adhesion between Cuprophan and other materials and between Cuprophan and itself. Thus, it is difficult to utilize improved hemodialyzer designs requiring leak-proof compartments which depend upon the membrane material for sealing off blood from dialysate solution and blood and dialysate solutions from the atmosphere.

The membranes prepared from the present invention are significantly improved over the state-of-the-art materials, e.g., Cuprophan in the following areas.

1. Polycarbonate membranes permit clearance of critical "middle molecules" up to 3 times greater than Cuprophan in comparable tests.

2. The burst strength of polycarbonate membranes is 1.5–2 times that of Cuprophan.

3. The latitude of membrane properties achievable with polycarbonates is considerable and can be arranged in accordance with clinical needs.

4. Polycarbonate membranes are stiffer than Cuprophan in the wet state. This property results in thinner blood layers in dialyzers, more efficient dialysis and lower blood priming volume.

5. Polycarbonates are heat-sealable wet or dry permitting wide latitude in dialyzer design.

6. Due to greater efficiency of dialysis with polycarbonate membranes, projections indicate a greatly reduced dialysis time (9 hrs/wk) compared with Cuprophan.

In attempting to develop hemodialysis membranes with mechanical and transport properties superior to those of Cuprophan, it has previously been proposed, by two of the present coinventors, to fabricate membranes of polyether-polycarbonate block copolymers containing a balance of hydrophobic aromatic polycarbonate blocks, which impart toughness, and hydrophilic polyether blocks, which impart water and solute permeability. The polycarbonate system was chosen for dialysis membrane development because of the outstanding mechanical properties shown by commercial polycarbonate, the very low thrombogenicity exhibited by properly heparinized polycarbonate surfaces, the ease of forming this polymer type into various configurations such as films and fibers, and the many synthetic possibilities for chemical modification of the basic aromatic polycarbonate backbone structure to achieve desired membrane transport properties. As disclosed in the "Proceedings of the 5th Annual Contractors' Conference of the Artificial Kidney Program of the National Institute of Arthritis and Metabolic Diseases", U.S. Department of Health, Education and Welfare (1972), pages 32–33, gelled membranes were prepared from polyether-polycarbonate block copolymers by means of the phase inversion technique, i.e., casting a solution of the copolymer in a suitable solvent onto a substrate surface to form a layer which is allowed to dry only partially and which is then immersed in a liquid gelation medium in which the copolymer is insoluble but which is miscible with the solvent, employing chloroform as the casting solvent and methanol as the gelation medium. The gelled membranes resulting from such procedure, while exhibiting considerable superiority over Cuprophan membranes in their permeabilities to solutes in the middle molecule range, were found, however, to possess several drawbacks to their practical use as hemodialysis membranes. First of all, their ultrafiltration rates were 2 to 5 times that of Cuprophan membranes, which would be clinically unacceptable for hemodialysis as presently administered due to the possibility of dehydration of the patient occurring during treatment. Secondly, their burst strength was no more, and in many cases, less than that of Cuprophan membranes. Thirdly, attempts at continuous casting of the membrane on production-type machinery in widths suitable for use in commercial hemodialyzers, presented further problems which rendered the methanol gelation procedure impractical for commercial hemodialysis membrane production.

The most serious problem encountered was the frequent occurrence of gross leakage of albumin through the membranes during ultrafiltration testing, and which was found to be attributable to holes or other imperfections in the ultrathin surface of the membrane which forms the barrier between the blood and the dialysate or flushing solution. All of these membranes are referred to as being "anisotropic" or "skinned", which means that their two sides are significantly different from each other, one side being relatively smooth and the other side being relatively rough and porous. The smooth side is the "barrier" layer which faces the blood during hemodialysis and is quite thin, on the order of 0.05 to 0.2 microns. The remainder of the membrane merely functions as a support structure and is about 25 to 30 microns in thickness. The integrity of the barrier layer is crucial to the performance of the membrane in dialysis. Any perforation, puncture or other compromise of the integrity of the barrier layer destroys the usefulness of the membrane and all materials in contact with the membrane merely leak through. It has now been proven by electron microscopy that the methanol-gelled polycarbonate membranes are formed with their barrier layer on the side of the membrane contacting the casting surface rather than the side of the membrane facing the air during drying. The significance of this fact is that continuous casting of these membranes on production-type machinery involves continuously peeling the delicate barrier layer off of the casting surface during the process, making it almost impossible to maintain the integrity of the barrier layer and obtain a membrane suitable for use in hemodialysis. Also, it was found that long term exposure of the membrane to methanol affects the membrane properties, thereby necessitating the quick and extensive flushing or washing of the membrane to remove the methanol therefrom and replace it with water in order for the membrane to have adequate shelf-life. One additional problem presented was the impracticality of employing large volumes of methanol as the gelation medium due to the cost, toxicity and flammability of this material.

Other membranes of polycarbonate type which have been found to be unsuited for hemodialysis are those suggested in British patent specification No. 1,395,530. See also Kesting, J. Macromol. Sci. (Chem), A4(3), pp. 655-664 (1970); U.S. Pat. Nos. 2,964,794, 3,031,328, 3,450,650, 3,526,588 and 3,655,591; and British patent specification No. 1,059,945.

It is therefore an object of the present invention to provide hemodialysis membranes having improved permeability to solutes in the middle molecule range as compared with presently available hemodialysis membranes, while maintaining low molecular weight solutes.

Another object of the invention is to provide hemodialysis membranes having improved burst and tear strengths as compared with presently available hemodialysis membranes.

A further object of the invention is to provide hemodialysis membranes having improved shelf-life as compared with presently available hemodialysis membranes. A further object of the present invention is to provide hemodialysis membranes having improved sealability over presently available hemodialysis membranes making possible leak-proof hemodialyzer compartments through simple heat-sealing of the membranes.

Still another object of the invention is to provide a process for producing gelled polycarbonate membranes useful for hemodialysis and having the improved properties as set forth in the preceding objects, which is easily and economically adaptable to large scale machine production without impairing the integrity of the barrier layer of the membrane.

The above and other objects are achieved in accordance with the present invention by producing a gelled polycarbonate membrane from a polyether-polycarbonate block copolymer by the phase inversion technique employing an aqueous gelation system with water as the gelling medium and a water-miscible organic solvent as the casting solvent. More specifically, the process comprises casting on to a substrate surface having a smooth finish, a layer of casting solution comprising a polyether-polycarbonate block copolymer containing from about 5 to about 35% by weight of the polyether component and a water-miscible organic solvent together with a cosolvent which acts as a swelling agent for the copolymer, drying the layer to partially evaporate the solvents therefrom, immersing the partially dried layer in water to form a gelled membrane, and stripping the resulting gelled membrane from the substrate surface.

It has been found that gelled polycarbonate membranes produced in this manner, with water as the gelling medium, are formed with their barrier layer on the side of the membrane facing the air during drying, rather than on the side of the membrane in contact with the casting surface as is the case with methanol-gelled polycarbonate membranes, which enables the gelled membrane to be readily stripped from the casting surface without impairing the integrity of the delicate barrier layer, thereby rendering large-scale machine production of such membranes practical. The use of water as a gelling medium in place of methanol also facilitates large scale machine production in that water is, of course, less expensive, non-toxic and non-flammable, and also eliminates the necessity for the extensive flushing or washing of the membrane to remove the gelling medium therefrom as was required in methanol gelation. It has also been found that the water-gelled polycarbonate membranes have considerably higher strength than either the methanol-gelled polycarbonate membranes or Cuprophan membranes. Gelled polycarbonate membranes fabricated in accordance with the present invention have furthermore been found to be considerably superior to Cuprophan membranes in their permeabilities to solutes in the middle molecule range while maintaining ultrafiltration rates and clearance of low molecular weight solutes comparable to that of Cuprophan membranes. Moreover, it has been found that the ultrafiltration rates of the membranes fabricated in accordance with the present invention are controllable to levels comparable to those of Cuprophan membranes by proper selection of the molecular weight of the polyether-polycarbonate block copolymer used in fabricating the membrane.

The polycarbonate material from which the improved hemodialysis membranes are fabricated in accordance with the present invention is a polyether-polycarbonate block copolymer preferably containing from about 5 to about 35% by weight of the polyether component. It has been found that this proportion of polyether blocks renders the normally hydrophobic polycarbonate sufficiently hydrophilic so as to make it suitable for use as a hemodialysis membrane. Certain of such block copolymers may be prepared, for example by the method of Goldberg (Journal of Polymer Science: Part C, No. 4, pp. 707-730 [1963] wherein a comonomer mixture of from about 95 to about 65% by weight of 2,2-(4,4'-dihydroxydiphenyl) propane, generally known as bisphenol A, and correspondingly from about 5 to about 35% by weight of a polyether glycol such as polyethylene glycol, is reacted with a carbonic acid derivative such as phosgene. A polyethylene glycol which is found to be particularly suitable is Carbowax 6000, which is a polyethylene glycol having an average molecular weight of 6700, although polyethylene glycols of other molecular weights can also be used, such as, for example, Carbowax 600, Carbowax 1000 and Carbowax 4000, which are polyethylene glycols having molecular weights of 600, 1000 and 4000, respectively. Polyether glycols other than polyethylene glycols can also be used, such as, for example, polypropylene oxide-polyethylene oxide block copolymers as exemplified by members of the Pluronic diol series such as Pluronic F68.

Preparation of the polyether-polycarbonate block copolymers is generally carried out by dissolving the comonomer mixture, together with pyridine as an acid acceptor, in a molar ratio to the monomers of approximately 3 to 1, in a suitable solvent such as dichloromethane to give a total solids content of approximately 5 to 16%, and adding phosgene gas to the solution with vigorous stirring. The polymerization temperature is preferably maintained within the range of 20° to 43° C. When crystals of pyridine hydrochloride begin to form, a chain terminator such as phenol is added in amounts up to about 0.5 mole % of the monomers, either in one portion or in several increments during the latter stages of the reaction. The rate of phosgene gas addition is generally maintained within the range of between 500 to 2,000 ml/min. up to the point at which the pyridine hydrochloride crystals form, and thereafter maintained within the range of about 100 to 600 ml/min. The formation of a permanent pale pink to pale brown color indicates completion of the reaction, at which point the copolymer is precipitated by mixing the polymerization mixture with, for example, isopropyl alcohol, hexane or an 80:20 by volume mixture of acetone and water. The precipitated polymer is thereafter ground to a hard crumb, washed with hot water and dried.

Polyether-polycarbonate block copolymers having molecular weights ranging from about 50,000 to about 750,000 may suitably be prepared in the above manner. A preferred range of molecular weights is from about 200,000 to about 500,000, since it has been found that membranes fabricated in accordance with the present invention from polyether-polycarbonate block copolymers having molecular weights within such preferred range exhibit ultrafiltration rates comparable to those of Cuprophan membranes and hence within the range clinically acceptable for use in hemodialysis. Regulation of molecular weight is generally effected by the rate of phosgene addition and by the addition of chain terminators. Furthermore, since impurities present in the reactant materials may tend to inhibit the formation of higher molecular weight polymers or catalyze the degradation of the polymer molecular weight, it is important to employ the reactant materials in as pure a form as possible. For example, in the case of bisphenol A, which is produced in several commercial grades, epoxy grade bisphenol A which has been further recrystallized from toluene to remove all phenol should be used. Still further preferred is the so called polycarbonate grade Bisphenol A.

Casting solutions for use in the process of the present invention are prepared by dissolving the polyether-polycarbonate block copolymer in a water-miscible organic solvent for the copolymer. The solvent preferably has a boiling point within the range of 50° to 85° C. for optimum room temperature casting. The preferred solvent is 1,3-dioxolane which has the appropriate combination of high solvent power for the copolymer, water-miscibility and a boiling point of 75° to 76° C. Other suitable solvents which can be employed include 1,3-dioxan, 1,4-dioxan, tetrahydrofuran, butyrolactone, acetonitrile, cellosolve acetate, dimethylformamide, pyridine and mixtures thereof. Chloroform, which was previously suggested for use as a casting solvent in the methanol-gelation of polycarbonate membranes, is not suitable since it is not water-miscible.

The casting solutions are generally formulated to have a total solids content of from about 1 to about 20 weight % to give dopes ranging in viscosity from about 5,000 to about 30,000 cps. Typically, solids contents range from about 10 to about 20 weight % to give viscosities of from about 7,000 to about 25,000 cps, the preferred range. A swelling agent, such as dimethyl sulfoxide, is advantageously added to the casting solution in amounts ranging from about 10 to about 75% by weight of the copolymer, the preferred range being from about 15 to about 25% by weight of the copolymer. The addition of the swelling agent has been found to enhance the permeability of the resulting membrane. Other swelling agents which have been employed include dimethylformamide, dimethylacetamide, acetamide, formamide and pyridine.

Production of the polycarbonate membrane can be effected on a continuous basis by doctor blade casting of the casting solution onto a moving surface having a smooth finish, such as a coated release paper. The well-filtered (10 $\mu$m) casting solution is preferably supplied to a hopper placed in front of the doctor blade by means of a positive displacement metering pump. The hopper is provided with end guides for controlling the width of the membrane sheet. The thickness of the membrane sheet is controlled by adjusting the gap between the knife and the moving belt surface, which is usually set so as to give a final membrane thickness of 1.0–1.5 mils.

The freshly cast and wet film is allowed to air dry at temperatures ranging from about 20° to about 30° C. for periods ranging from about 1.0 to about 5.0 minutes to partially evaporate the solvent therefrom, the drying time being determined by both the belt speed and the drying distance. The partially dried film is gelled to produce the final membrane by immersion, while still adhering to the moving belt, in a water bath. The gelation bath temperature may be varied between about zero to about 40° C., the preferred range being 20° to 30° C. After gelation, the membrane is peeled from the moving belt and rolled up separately from the belt onto a cylindrical core. The membrane is finally washed thoroughly with deionized water to remove the last traces of solvent and swelling agent and stored in a sealed plastic bag or other container containing water and a sterilant such as formaldehyde. The final thickness of the membrane generally varies from about 1.0 to 1.5 mils, depending upon the knife gap setting, casting solution viscosity and belt speed.

The following examples are given for the purpose of illustrating the present invention.

EXAMPLE 1

This example illustrates a preferred procedure for preparing a polyether-polycarbonate block copolymer for use in fabricating membranes in accordance with the present invention.

Into a solution of 360 gm (1.58 moles) of 2,2-(4,4'-dihydroxydiphenyl)propane (bisphenol A), 120 gm (0.02 mole) of poly(ethylene glycol) of average molecular weight 6700 (Carbowax 6000, Union Carbide Corporation), 384 mls (4.77 moles) of pyridine and 2700 mls of dichloromethane, was added with vigorous stirring phosgene gas at a rate of 570 mls/min. The temperature of the mixture was maintained at 25°±0.5° C. by means of an ice water bath. After 90 minutes, crystals of pyridine hydrochloride formed, at which point a solution of 0.3 gm (0.0031 mole) of phenol in 12 mls of dichloromethane was added. The polymerization reaction was allowed to continue at the same rate of phosgene addition until the formation of a permanent pale pink color was observed, which indicated completion of the reaction (an additional 70 minutes). The polymer was precipitated by stirring the very viscous polymerization mixture with a solution of 5178 mls of acetone, 1290 mls of water and 298 mls of concentrated hydrochloric acid. The gelatinous solid was ground to a hard crumb with hot water in a large Waring blender, collected on a filter and washed with hot water. After drying the yield of white copolymer was 496 gm (95% yield). The polymer was found by infrared analysis to contain 25 weight % of polyether component and have an intrinsic viscosity of 1.7 (0.5% w/v in trichloromethane, 25.0° C.), corresponding to a molecular weight of 377,000.

Further syntheses of the basic polycarbonate copolymer were carried out for a variety of purposes, including (1) production membrane casting, (2) control of average molecular weight and molecular weight distribution, (3) improvement of polymer isolation and purification technique, and (4) polymer and casting solution stability studies. For all of the syntheses polycarbonate-grade bisphenol A was used.

The objective of these studies was to determine those experimental parameters which, during the polymerization reaction, affected the final polymer average molecular weight and molecular weight distribution. Polymer average molecular weight was previously found to influence membrane permeability characteristics as well as affecting the viscosity of the casting solution. The effect of molecular weight distribution on membrane properties is considered important in the processing of the casting solution. Specifically, the presence of a small, very high molecular weight fraction of the polymer appears to be responsible for difficulty in filtration of the casting solution. Consequently, control of polymer molecular weight characteristics is not only important for achieving batch-to-batch uniformity in the synthesis and quality control of membrane properties, but also is significant as regards scaling up of membrane production.

A series of additional polymerizations were carried out to determine the relative effects of varying the rate of addition of the reagents and the addition of chain terminators on polymer viscosity average molecular weight. Phosgene addition rate was monitored by means of a rotometer and measurements were relative only; chain stopper was added to the polymerization mixture immediately after the appearance of pyridine hydrochloride crystals. The polymerizations were allowed to run to completion and the polymers isolated by the same procedure in each case. The results indicate that regulation of phosgene addition rate during the latter stages of the polymerization as well as addition of chain terminator is effective in controlling final polymer molecular weight. Varying the amount of chain terminator with other parameters held constant is seen to have varied final molecular weight. Finally, low phosgene rate and the absence of chain terminator is seen to favor maximum molecular weight. Polymerization temperature is also expected to affect polymer viscosity.

A number of one pound polymerizations were also carried out to provide polymer for membrane casting and process studies. There was only slight variation from run to run in mode of phosgene and chain terminator addition, but the same workup procedure was employed in each case. The temperature in each polymerization was maintained at 25°±1° C. In spite of some variation in reaction conditions, almost all polymer viscosities (5% $CHCl_3$ solutions) fell within the 70–100 cps range. Yields of purified, vacuum-dried polymer ranged from 90–96%.

The crude polymer is in a highly-swollen, finely-divided state (ideally in solution) during the critical washing stages of the workup which is preliminary to membrane fabrication. Specifically, the crude reaction mixture is poured with stirring into acidified aqueous acetone. The polymer is then coagulated and ground to a hard crumb in a blender and finally washed thoroughly with water. Four modifications to this procedure were carried out, together with original procedure itself as a control, to study the comparative effectiveness of purification on viscosity, color, particle size, and impurity levels of the resulting polymer. Samples were taken from the same bath of crude polymerization reaction mixture for this study.

Modification 1

The crude polymer solution from the polymerization reaction was first washed with dilute hydrochloric acid, then dumped into the coagulating medium in a blender. It was thought that exposure to acid via liquid-liquid contact would extract pyridine (as the hydrochloride) more efficiently. The resultant polymer was finely divided and pure white.

Modification 2

The crude polymer was coagulated in isopropyl alcohol (IPA) containing hydrochloric acid, then stirred in a blender with more IPA. The remainder of the procedure was normal. The resultant polymer was in the form of a fine crumb and had a pale straw color.

Modification 3

The normal procedure was followed through the coagulation step, then a cold deionized water wash in the blender was carried out to further encourage pyridine hydrochloride extraction before deswelling. The resultant polymer was white but coarser than that obtained in Modification 1.

Modification 4

The coagulation procedure described in Modification 3 was used and the polymer was then ground and washed with IPA. The resultant polymer was pale staw-colored.

Viscosities, total pyridine (free plus hydrochloride) content and chloride ion content were measured on the polymers obtained from each of the above modified workups as well as that from the standard workup. The results are shown below.

| Workup Procedure | Viscosity of 5% $CHCl_3$ sol'n, cps (25° C.) | ppm Total Pyridine | ppm $Cl^-$ |
|---|---|---|---|
| Standard | 79.3 | 2300 | 42 |
| Modification 1 | 88.0 | 6300 | 49 |
| Modification 2 | 81.8 | 2600 | 34 |
| Modification 3 | 82.0 | 4900 | 33 |
| Modification 4 | 56.4 | 1300 | 16 |

None of the above modified workup procedures produced a net improvement over the standard procedure. Slurrying the swelled polymer with IPA (Modification 4) removed more pyridine and pyridine hydrochloride but resulted in discolored polymer with substantially reduced viscosity (apparently due to alcoholysis).

The standard workup procedure is seen to inadequately remove pyridine and pyridine hydrochloride from the polymer. Further reducing the level of these impurities by 1–2 orders of magnitude was thus felt to be necessary. Each of two additional purification steps in the workup procedure was investigated and found to be superior to the first four.

The results of these purification methods are summarized below.

| Polymer | Additional Purification | 25° C. [η] $CHCl_3$ | ppm Total Pyridine | ppm $Cl^-$ |
|---|---|---|---|---|
| P-7-92 | None | 1.59 | 2300 | 42 |
| P-7-92 RP | Reprecipitation | 1.51 | 2300 | 15 |
| P-7-107 B | Acid wash and aqueous extraction | 1.78 | 600 | 13 |

The acid wash followed by extensive liquid-liquid extraction with water was the more effective technique in substantially reducing both total pyridine and pyridine hydrochloric levels over those of the standard workup procedure. Reprecipitation effectively reduced pyridine hydrochloride content but not total pyridine and resulted in a slight reduction in polymer viscosity.

In the present polymer processing technique, wet purified polymer is air-dried 48 hours followed by final vacuum drying at 60° C. for 1 hour.

For further reference, compare the five following reports to the National Institutes of Health, hereby expressly incorporated by reference and relied upon:

[1] Modified Polycarbonate Membranes for Hemodialysis. National Institute of Scientific Research, Rancho Santa Fe, Calif. Ann. Rept. 1 July 70–31 Dec. 71. PB-213 160/6. This document was received in NTIS (National Technical Information Service) in January, 1973, and was announced in the bi-weekly journal, GRA, Number 2, dated Jan. 25, 1973.

[2] Modified Polycarbonate Membranes for Hemodialysis. National Institute of Scientific Research, Rancho Santa Fe, Calif. Ann. Rept. 1 Jan-31 Dec. 72. PB-225 043/9. This document was received in NTIS in January, 1974, and was announced in the bi-weekly journal, GRA, Number 3, dated February 8, 1974.

[3] Modified Polycarbonate Membranes for Hemodialysis. National Institute of Scientific Research, Rancho Santa Fe, Calif. Rept. 15 Jun-20 Sep 69. PB-225 135/3. This document was received in NTIS in December, 1973, and was announced in the bi-weekly journal, GRA, Number 2, dated Jan. 25, 1974.

[4] Modified Polycarbonate Membranes for Hemodialysis. National Institute of Scientific Research, Rancho Santa Fe, Calif. Ann. Rept. 1 Aug 73–31 Mar 74. PB-233 669/1. This document was received in NTIS in August, 1974, and was announced in the bi-weekly journal, GRA, Number 18, dated Sept. 6, 1974.

[5] Modified Polycarbonate Membranes for Hemodialysis. National Institute of Scientific Research, Rancho Santa Fe, Calif. National Institute of Arthritis and Metabolic Diseases, Bethesda, Md. Ann. Rept. 1 Jan-31 Jul 73. PB-235 792/9SL. This document was received in NTIS in October, 1974, and was announced in the bi-weekly journal, GRA, Number 24, dated Nov. 29, 1974.

EXAMPLE 2

A mixture of 491 gm of the polyether-polycarbonate block copolymer obtained by reacting phosgene with a comonomer mixture of bisphenol A (75 wt %) and Carbowax 6000 (25 wt %), and having an intrinsic viscosity of 1.7 (in chloroform at 25° C.) corresponding to a molecular weight of 377,000, 3146 gm of 1,3-dioxolane and 98.2 gm of dimethyl sulfoxide, was slowly agitated until solution was effected (approximately 8 hours). The crude solution was filtered in a pressure filter at 30 to 50 psig through a polypropylene felt or 25 μm porosity asbestos sheet medium to remove a small residue of fine insoluble matter. The resulting casting solution has a viscosity of 16,000 cps at 25° C.

Approximately one-half gallon of the above 10 μm filtered casting solution was cast via a doctor blade onto the surface of a 16-inch wide moving belt moving at a speed of 2.36 feet per minute. The hopper end guides were set to provide a cast film width of 15½ inches and the gap between the doctor knife and the moving belt surface was set at 7.0 mils. These dimensions provide samples suitable for use in the Kiil dialyzer. A total drying time of the cast film of 2.54 minutes was allowed before gelation in a water bath. The ambient air temperature was maintained at 24.7°±0.4° C. and the gelation water bath temperature at 25°±0.5° C. After gelation, the resulting membrane was peeled from the moving belt and rolled up separately from the belt onto a cylindrical core. A total of 177 feet of membrane was thus produced during a period of 75 minutes. The membrane was washed in a flowing stream of deionized water and stored in a sealed polyethylene bag containing 2% aqueous formaldehyde.

The polycarbonate membrane fabricated as above was found to have physical and permeability properties as set forth in Table 1, below. For purposes of comparison, corresponding values are given for a typical sample of Cuprophan PT150 membrane. The permeability properties were determined in a dialysis test cell of the type designed by the National Bureau of Standards.

TABLE 1

| | Polycarbonate Membrane of Example 1 | Cuprophan PT 150 Membrane |
|---|---|---|
| Wet Thickness, mils | 1.3 | 0.9 |
| Relative Burst Strength, Cm Hg. | 30 | 20 |
| Ultrafiltration Rate at 37° C. 200 mm Hg ΔP, ml/$m^2$-hr-mm Hg | 3.6 | 3.9 |
| Diffusive permeability at 37° C. cm/min (× $10^4$) (Solute molecular weight in parenthesis) | | |
| Sodium chloride (58.4) | 709 | 707 |
| Vitamin $B_{12}$(1355) | 101 | 46 |
| Human Serum Albumin (60,000) | 0 | 0 |

It can be seen from the data in Table 1 that the polycarbonate membrane fabricated in accordance with the present invention, with approximately 40% greater thickness than the Cuprophan membrane, and approximately the same ultrafiltration rate and permeability towards sodium chloride, a representative low molecular weight solute in blood, exhibits a 50% higher burst strength and a 120% higher permeability toward Vitamin $B_{12}$, a model medium molecular weight solute, while being completely impermeable to serum albumin, a high molecular weight component of blood whose removal from the blood during hemodialysis is not desirable.

It has further been found that the polycarbonate membrane prepared in accordance with the present invention is considerably stiffer in its wet state than Cuprophan membranes. This is of importance in hemodialysis in maintaining a thin blood film, a greater area of blood for dialysis, and a low blood priming volume.

Also, the polycarbonate membrane of the present invention is heat sealable, making possible greater latitude in hemodialyzer design. Furthermore, the polycarbonate membrane of the present invention has proven to be non-toxic in a battery of in vitro and animal tests, is blood compatible, and its thrombogenicity is approximately the same as Cuprophan membranes in vitro.

Examination of the polycarbonate membrane prepared in accordance with Example 2, employing water as a gelation medium, by scanning electron photomicrography showed the side of the membrane which was facing the air during drying to be smoother and more regular than the side of the membrane which was in contact with the casting surface, indicating that the membrane was formed with its barrier or active layer on the side of the membrane facing the air during drying rather than on the side of the membrane in contact with the casting surface as was the case with methanol-gelled polycarbonate membranes. Hence, the continuous peeling of the membrane from the moving belt surface has no deleterious effect on the delicate barrier layer of the membrane, making large scale machine production of the membrane feasible. The water-gelled polycarbonate membrane prepared in accordance with Example 1 also appeared to have a much finer and more uniform ultragel structure than a similar membrane prepared by methanol gelation. This is reflected in the considerably higher strength of the water-gelled polycarbonate membranes, which were found to have burst strength 50 to 70% greater than the corresponding methanol-gelled polycarbonate membrane.

Hence, it can be seen that the process of the present invention enables large scale machine production of polycarbonate membranes which are useful for hemodialysis and which exhibit improved strength and improved permeabilities to solutes in the middle molecule range as compared with presently available hemodialysis membranes, while maintaining ultrafiltration rates within the clinically acceptable range to avoid dehydration and also maintaining clearance of low molecular weight solutes within the clinically acceptable range to avoid low molecular weight depletion syndrome.

[EXAMPLE 3]

[This example shows the efficacy of swelling agent added to the casting solution formulation in enhancing the water and solute permeability of polycarbonate membranes prepared according to the present invention.]

[Gelled membranes were cast under identical conditions from casting formulations containing a polyether-polycarbonate block copolymer obtained by reacting phosgene with a comonomer mixture of bisphenol A (75 wt %) and Carbowax 6000 (25 wt %) and having an intrinsic viscosity of 1.3 (in chloroform at 25° C.), corresponding to a mol. wt of 190,000. The casting solution formulations contained varying amounts of the swelling agent dimethyl sulfoxide (DMSO). The properties of the resultant polycarbonate membranes as a function of the amount of DMSO swelling agent in the casting formulation are summarized in Table 2. Corresponding values for a typical sample of Cuprophan PT-150 are given for comparison.]

TABLE 2

| MEMBRANE | POLYCARBONATE MEMBRANES of Example 3 | | | CUPROPHAN PT150 MEMBRANE |
|---|---|---|---|---|
| Grams of DMSO per 15 Grams of Polymer in Casting Solution | 0 | 2 | 4 | — |
| Wet Thickness, Mils | 1.0 | 1.2 | 1.7 | 0.9 |
| Water Content, % to Dry Wt. | 40 | 72 | 113 | 103 |
| Ultrafiltration Rate at 25° C. 600 mm HgΔP, ml/m$^2$ - hr - mmHg | 1.60 | 4.73 | 10.4 | 1.99–3.9 |
| Diffusive Permeability, at 25° C. cm/min (× 10$^4$)(Soluble molecular weight in parenthesis) | | | | |
| Sodium Chloride (58.4) | 370 | 507 | 541 | 460 |
| Urea (60.1) | 418 | 519 | 531 | 438 |
| Creatinine (113.1) | 223 | 299 | 316 | 232 |
| Uric Acid (168.1) | 192 | 249 | 254 | 162 |
| Phosphate | 97 | 159 | 194 | 126 |
| Raffinose (504.4) | 71 | 102 | 126 | 62 |
| Inulin (5200) | 5 | 13 | 22 | 4 |
| Human Serum Albumin (60,000) | 0 | 0 | 0 | 0 |

[The data of Table 2 clearly show the marked effect of adding DMSO to the casting solution on the degree of membrane swelling, as measured by membrane wet thickness and water content, with resultant enhancement of membrane permeability to water and a variety of solutes. The polycarbonate membrane prepared using the casting formulation containing no swelling agent exhibited permeability properties comparable to those of a typical Cuprophan PT150 membrane. Addition of the first increment of DMSO swelling agent (2 grams per 15 grams of polymers) to the casting formulation is seen to have nearly doubled the water content and tripled the hydraulic permeability (as measured by ultrafiltration rate) of the membrane, and increased the permeability to all the solutes tested. The degree of permeability enhancement increased with solute molecular size, with 24–37% higher values observed with the smaller solutes, such as urea and creatinine, and a very marked increase of 160% found for inulin, a model solute representative of the upper "middle molecule" range. Further increase in the level of swelling agent in the casting formulation (to 4 grams per 15 grams of polymer) is seen to have still further increased the polycarbonate membrane water content and water permeability, only slightly (2–7%) increased smaller solute permeability (i.e. sodium chloride, urea, creatinine and uric acid), while still resulting in a substantial increase in "middle molecule" permeability (22, 24 and 69% increase for phosphate, raffinose and inulin respectively). Significantly, the polycarbonate membranes completely reject albumin even when substantial amounts of swelling agent are added to the casting formulation.]

EXAMPLE [4] *3*

This example serves to illustrate the effectiveness of several cosolvents —swelling agents for enhancing polycarbonate membrane permeability when added to the membrane casting solution formulation.

Casting solutions were prepared from the following formulation, using a polyether-polycarbonate block copolymer obtained by reacting phosgene with a comonomer mixture of bisphenol A (75 wt %) and Carbowax 6000 (25 wt %) and having an intrinsic viscosity (in chloroform at 25° C.) of 1.52 corresponding to a molecular weight of 301,000.

| COMPONENT | WEIGHT-GRAMS |
|---|---|
| Polyether-Polycarbonate Block Copolymer | 40.0 |
| 1,3-Dioxolane | 256.2 |
| Swelling Agent | 8.0 |

Membranes were prepared from each formulation by hand casting under identical conditions on glass plates at room temperature and gelling in water at 25° C. after varying drying periods. The physical and permeability properties found for these membranes are shown in Table [3] *2*.

[TABLE 3] *TABLE 2*

| Formulation | 1 | | 2 | | 3 | |
|---|---|---|---|---|---|---|
| Swelling Agent | Pyridine | | Dimethyl Formamide | | Dimethyl Sulfoxide | |
| Viscosity, cps at 25° C. | 8570 | | 8090 | | 8500 | |
| Dry Time, Minutes | MEMBRANE PROPERTIES | | | | | |
| 1.75 | 1.54<br>40.3 | 3.51<br>538 | 1.48<br>42.4 | 4.14<br>648 | 1.60<br>41.5 | Sample Underdried |
| 2.00 | 1.38<br>44.4 | 2.65<br>597 | 1.46 | 3.55<br>548 | 1.48<br>39.1 | 3.79<br>597 |
| 2.25 | 1.36<br>41.7 | 3.14<br>601 | 1.35<br>41.1 | 2.87<br>613 | 1.38<br>42.0 | 3.35<br>516 |

U.F. rate (37° C., 200 mm), ml/m$^2$-hr-mm Hg.
Na Cl Permeability (37° C.), cm/min ($\times 10^4$)

*Key:
Thickness, mils
Burst Strength, cm Hg.

The data outlined in Table [3] *2* indicate that, after appropriate adjustment of drying time before gelation, polycarbonate membranes of equivalent strength and premeability characteristics can be prepared through formulation with any one of the three swelling agents, pyridine, dimethyl formamide and dimethyl sulfoxide.

What is claimed is:

1. A process for producing a polycarbonate membrane useful for hemodialysis which comprises casting on to a substrate surface having a smooth finish a layer of casting solution comprising a polyether-polycarbonate block copolymer having a molecular weight within the range of from about 50,000 to about 750,000 as determined by the intrinsic viscosity measurement and containing from about 5 to about 35% by weight of repeating alkylene ether units and correspondingly from about 95 to about 65% by weight of repeating bisphenol A-carbonate units and a water-miscible organic solvent together with a cosolvent which acts as a swelling agent for said copolymer, drying said layer to partially evaporate the solvents therefrom, immersing said partially dried layer in water to form a gelled membrane, and stripping said gelled membrane from said substrate surface.

2. The process of claim 1 wherein said polyetherpolycarbonate block copolymer has a molecular weight within the range of from about 200,000 to about 500,000 as determined by the intrinsic viscosity measurement.

3. The process of claim 1 wherein said polyetherpolycarbonate block copolymer comprises the polymerization reaction product of phosgene with a mixture of from about 95 to about 65% by weight of bisphenol A and correspondingly from about 5 to about 35% by weight of a polyethylene glycol, having a molecular weight in the range of 600 to 6,000.

4. The process of claim 1 wherein said solvent has a boiling point in the range of from about 50° to about 85° C.

5. The process of claim 1 wherein said solvent comprises 1,3-dioxolane.

6. The process of claim 1 wherein said casting solution contains from about 1 to about 20 weight % of total solids and has a viscosity within the range of from about 5,000 to about 30,000 cps.

7. The process of claim 1 wherein said casting solution contains from about 10 to about 20 weight % of total solids and has a viscosity within the range of from about 7,000 to about 25,000 cps.

8. the process of claim 1 wherein said cosolvent-swelling agent is present in said casting solution in amounts ranging from about 10 to about 75% by weight based on the weight of said copolymer.

9. The process of claim 8 wherein said cosolvent-swelling agent is present in amounts ranging from about 15 to about 25% by weight based on the weight of said copolymer.

10. The process of claim 8 wherein said cosolvent-swelling agent is selected from the group consisting of dimethyl sulfoxide, dimethyl formamide and pyridine.

11. The process of claim 8 wherein said cosolvent-swelling agent comprises dimethyl sulfoxide.

12. The process of claim 1 wherein the layer of casting solution is air-dried at temperatures ranging from about 20° to about 30° C. for a period ranging from about 1.0 to about 5.0 minutes prior to being immersed in said water.

13. The process of claim 1 wherein said water is maintained at a temperature ranging from about 20° to about 30° C.

14. The polycarbonate membrane produced in accordance with the process of claim 1.

15. The polycarbonate membrane of claim 14 wherein said polyether-polycarbonate block copolymer has a molecular weight within the range of from about 200,000 to about 500,000 as determined by the intrinsic viscosity measurement.

16. A process for producing a polycarbonate membrane useful for hemodialysis which comprises casting onto a substrate surface having a smooth finish a layer of casting solution comprising a polyether-polycarbonate block copolymer having a molecular weight within the range of from about 50,000 to about 750,000 as determined by the intrinsic viscosity measurement and containing from about 5 to about 35% by weight of repeating alkylene ether units and correspondingly from about 95 to about 65% by weight of repeating bisphenol A-carbonate units and a water-miscible organic solvent together with a cosolvent which acts as a swelling agent for said copolymer, drying said layer to partially evaporate the solvents therefrom, immersing said partially dried layer in water to form a gelled membrane, and stripping said gelled membrane from said substrate surface.

17. A process for producing a polycarbonate membrane useful for hemodialysis which comprises producing a polyether-polycarbonate block copolymer having a molecular weight within the range of from about 50,000 to about 750,000 as determined by the intrinsic viscosity measurement and containing from about 5 to about 35% by weight of repeating alkylene ether units and correspondingly from about 95 to about 65% by weight of repeating bisphenol A-carbonate units, the method for producing said polyether-polycarbonate block copolymer comprising dissolving a polyether glycol compound, bisphenol A, and pyridine in a solvent to give a total solids content of about 5 to about 16%, by weight, reacting the dissolved bisphenol A, polyether glycol compound, and pyridine with phosgene by adding phosgene, at an initial feed rate, to said solution with vigorous stirring while maintaining the solution in the temperature range of about 20° C. to about 43° C. until crystals of pyridine hydrochloride begin to form, thereafter adding a chain terminator to the reacted solution and reducing the phosgene feed rate to about one-fifth of initial phosgene rate until the reaction solution undergoes a permanent color change, forming a casting solution comprising said polyether-polycarbonate block copolymer dissolved in a solution comprising a water-miscible organic solvent together with a cosolvent, said cosolvent acting as a swelling agent for said copolymer, casting a layer of said casting solution onto a substrate surface having a smooth finish, drying said layer to partially evaporate the solvents therefrom, immersing said partially dried layer in water to form a gelled membrane, and stripping said gelled membrane from said substrate surface.

18. The process of claim 17 wherein the polyether-polycarbonate block copolymer has a molecular weight of from about 200,000 to about 500,000 as determined by intrinsic viscosity measurement and the polyether glycol compound is chosen from the group consisting of polythylene glycol and polypropylene oxide-polyethylene oxide block copolymers.

19. The process of claim 17 wherein the bisphenol A, polyether glycol and pyridine are dissolved in a halogenated alkane.

20. The process of claim 19 wherein the halogenated alkane is dichloromethane.

21. The process of claim 17 wherein about 3 moles of pyridine are present for each mole of bisphenol A and polyether glycol.

22. The process of claim 17 wherein the chain terminator is phenol.

23. The process of claim 17 wherein the precipitated polymer is additionally ground to a hard crumb, washed with hot water and dried.

24. The process of claim 17 wherein the bisphenol A is of a grade chosen from the group consisting of epoxy grade bisphenol A which has been further recrystallized from toluene and polycarbonate grade bisphenol A.

25. The process of claim 17 wherein the initial feed rate of phosgene is from about 500 ml/min to about 2000 ml/min.

* * * * *